United States Patent
Zhao et al.

(10) Patent No.: US 12,419,887 B2
(45) Date of Patent: Sep. 23, 2025

(54) TRANSITIONING PATIENTS TREATED FOR PULMONARY ARTERIAL HYPERTENSION TO SELEXIPAG

(71) Applicant: ACTELION PHARMACEUTICALS LTD, Allschwil (CH)

(72) Inventors: Carol Zhao, Titusville, NJ (US); Johanna Colvin Riesen, Titusville, NJ (US); Gary Arnold Palmer, Titusville, NJ (US); Michael Keating, Fairview, NC (US); Brian Hartline, San Diego, CA (US); Wade Benton, Redwood City, CA (US); Camelia Dumitrescu, San Francisco, CA (US); Mehul Bipinchandra Shah, Titusville, NJ (US)

(73) Assignee: Actelion Pharmaceuticals Ltd., Allschwil (CH)

( * ) Notice: Subject to any disclaimer, the term of this patent is extended or adjusted under 35 U.S.C. 154(b) by 965 days.

(21) Appl. No.: 17/612,014

(22) PCT Filed: May 20, 2020

(86) PCT No.: PCT/EP2020/064089
§ 371 (c)(1),
(2) Date: Nov. 17, 2021

(87) PCT Pub. No.: WO2020/234361
PCT Pub. Date: Nov. 26, 2020

(65) Prior Publication Data
US 2022/0257594 A1    Aug. 18, 2022

Related U.S. Application Data

(60) Provisional application No. 62/850,792, filed on May 21, 2019.

(51) Int. Cl.
*A61K 31/4965* (2006.01)
*A61K 45/06* (2006.01)
*A61P 9/12* (2006.01)

(52) U.S. Cl.
CPC .......... *A61K 31/4965* (2013.01); *A61K 45/06* (2013.01); *A61P 9/12* (2018.01)

(58) Field of Classification Search
None
See application file for complete search history.

(56) References Cited

U.S. PATENT DOCUMENTS

| | | | |
|---|---|---|---|
| 7,205,302 B2 | 4/2007 | Asaki et al. | |
| 8,791,122 B2 | 7/2014 | Hideyuki | |
| 9,284,280 B2 | 3/2016 | Itou | |

(Continued)

OTHER PUBLICATIONS

Frost et al., The Journal of Heart and Lung Transplantation, vol. 38, Issue 1, 2019 (published online Sepbemter 12 2018), pp. 43-50 (Year: 2018).*

(Continued)

*Primary Examiner* — Jeffrey S Lundgren
*Assistant Examiner* — Anthony Joseph Seitz
(74) *Attorney, Agent, or Firm* — BakerHostetler

(57) ABSTRACT

The present disclosure provides methods of transitioning a patient being treated for pulmonary arterial hypertension with a non-selexipag prostacyclin pathway agent (PPA) to selexipag.

5 Claims, 3 Drawing Sheets

(56) References Cited

U.S. PATENT DOCUMENTS 9,340,516 B2  5/2016  Itou
9,440,931 B2  9/2016  Nakamichi et al.

OTHER PUBLICATIONS

Frost et al., The Journal of Heart and Lung Transplantation, vol. 38, Issue 1, 2019 (published online Sep. 12, 2018), pp. 43-50 (Year: 2018).*
Frost et al., The Journal of Heart and Lung Transplantation, vol. 38, Issue 1, 2019 (published online Sep. 12, 2018), pp. 43-50 Supplemental Information (Year: 2018) (Year: 2018).*
Robert P. Frantz; Advances in Pulmonary Hypertension Jan. 1, 2017; 15 (4): 193-197 (Year: 2012).*
Anonymous, "Selexipag (Uptravi) for Pulmonary Arterial Hypertension", Medical Letter on Drugs and Therapeutics, New Rochelle, NY, US, vol. 58, No. 1488, Feb. 15, 2016, pp. 21-22.
Chakinala et al., "Real-World Dosing And Titration Of Selexipag In Patients With Pulmonary Arterial Hypertension In The Sphere Registry (Selexipag: The Users Drug Registry): Interim Analysis," PHA, PHA 2018 International PH Conference And Scientific Sessions, Ju. 29-Jul. 1, 2018, Orlando, Florida, Abstract, 2 pages.
Chakinala et al., "Real-World Dosing And Titration Of Selexipag In Patients With Pulmonary Arterial Hypertension In The Sphere Registry (Selexipag: The Users Drug Registry): Interim Analysis," Poster Presented At The American Thoracic Society International Conference; May 18-23, 2018; San Diego, CA, 1 page.
Chin et al., "Clinical Course of Patients Transitioned from Another Prostacyclin Pathway Agent to Selexipag in Sphere", Presented at the International Society for Heart and Lung Transplantation 39th Annual Meeting, Apr. 2019, 1 page.
Chin et al., "Clinical Course of Patients Transitioned from Another Prostacyclin Pathway Agent (PPA) to selexipag in Sphere," Abstract, Target Congress: International Society of Heart and Lung Transplantation, 2019, 1 page.
Faber et al., "Risk Assessment at Baseline and One Year in Patients with Pulmonary Arterial Hypertension (PAH): Data from the First 250 Patients Enrolled in Sphere (Uptravi@ [SelexiPag]: the users drug registry)", Poster presented at the American Thoracic Society International Conference; May 17-22, 2019; Dallas, TX, USA, 1 page.
Faber et al., "Risk Assessment at Baseline and One Year in Patients with Pulmonary Arterial Hypertension (PAH): Data from the First 250 Patients Enrolled in Sphere(Uptravi@ [SelexiPag]: the users drug registry)," Abstract, Target congress: American Thoracic Society, 2019, 3 pages.
Franco-Palacios et al., "Tolerability and Efficacy of Selexipag in Real Life Clinical Setting", CHEST Annual Meeting, Oct. 2017, 1 page.
Frost et al., "Safety and Tolerability of Transition from Inhaled Treprostinil to Oral Selexipag in Pulmonary Arterial Hypertension: Results from the TRANSIT-1 Study", Journal of Heart and Lung Transplatation, Jan. 2019, vol. 38, No. 1, pp. 43-50.
Hemnes et al., "Interim Analysis of Pulmonary Arterial Hypertension (PAH)-Targeted Background Therapy in Sphere (SelexiPag: The Users Drug Registry)", PVRI; Barcelona, Spain; Jan. 31-Feb. 3, 2019, Abstract, 2 pages.
Hemnes et al., "Pulmonary Arterial Hypertension-Targeted Background Therapy In SPHERE (Selexipag: The Users Drug Registry): Interim Analysis," Presented At PVRI; Barcelona, Spain; Jan. 31-Feb. 3, 2019, 1 page.
Hemnes et al., "Transitions From Inhaled, Intravenous, Subcutaneous, Or Oral Prostacyclin Pathway Agents To Selexipag: Interim Data From The Sphere Registry (Selexipag: The Users Drug Registry)," Poster Presented At The American Thoracic Society International Conference; May 18-23, 2018; San Diego, CA, 1 page.
Hemnes et al., "Transitions From Inhaled, Intravenous, Subcutaneous, Or Oral Prostacyclin Pathway Agents To Selexipag: Interim Data From The Sphere Registry (Selexipag: The Users Drug Registry)," Poster Presented At PHA 2018 International PH Conference And Scientific Sessions; Jun. 29-Jul. 1; 2018, Orlando, Florida, 1 page.
Hemnes et al., "Transitions From Inhaled, Intravenous, Subcutaneous, Or Oral Prostacyclins To Selexipag: Interim Data From The Sphere Registry (Selexipag: The Users Drug Registry)," Abstract, PHA, 2018, 2 pages.
Highland et al., "Characteristics Of Patients With CTD-Associated PAH Treated With Selexipag In The Real-World Setting: Interim Data From The Sphere Registry," Abstract, PVRI, 2019, 2 pages.
Highland et al., "Characteristics Of Patients With CTD-Associated PAH Treated With Selexipag In The Real-World Setting: Interim Data From The Sphere Registry," Slides Presented At PVRI, 2019, 25 pages.
Highland et al., "Clinical Course Of Patients Enrolled In SPHERE (Selexipag: The Users Drug Registry), A US Pulmonary Arterial Hypertension (PAH) Registry: One-Year Follow-Up," Abstract, Target Congress: American Thoracic Society, 2019, 2 pages.
Highland et al., "Clinical Course Of Patients Enrolled In SPHERE (Selexipag: The Users Drug Registry), A US Pulmonary Arterial Hypertension (PAH) Registry: One-Year Follow-Up", Poster Presented At The American Thoracic Society International Conference; May 17-22, 2019, 1 page.
Kimmig et al., "Successful Outpatient Transition From Intravenous Treprostinil To Oral Selexipag : D49. Surfing Safari: Case Reports In Pulmonary Vascular Medicine II", American Journal Of Respiratory And Critical Care Medicine, American Thoracic Society International Conference Abstracts, May 23, 2018, p. D49,.
McLaughlin et al., "Baseline And Demographic Data For The First 250 Patients From SPHERE (Uptravi®) [Selexipag]: The Users Drug Registry)," Poster Presented At PHA 2018 International PH Conference And Scientific Sessions; Jun. 29-Jul. 1; 2018, Orlando, Florida, 1 page.
McLaughlin et al., "Baseline And Demographic Data For The First 250 Patients From Sphere (Uptravi® [Selexipag]: The Users Drug Registry)," Poster Presented At The American Thoracic Society International Conference; May 18-23, 2018; San Diego, CA, 1 page.
McLaughlin et al., "Characterizing Patients Treated With Macitentan For Pulmonary Arterial Hypertension (PAH) In The U.S. Opsumit Users Registry (OPUS)," Abstract, PHA, ISPOR 2019, 1 page.
McLaughlin et al., "Interim Analysis Of Pulmonary Arterial Hypertension (PAH)-Targeted Background Therapy In Sphere (Selexipag: The Users Drug Registry)," Abstract, Target Congress: European Respiratory Society, 2018, 1 page.
McLaughlin et al., "Pulmonary Arterial Hypertension-Targeted Background Therapy In Sphere (Selexipag: The Users Drug Registry): Interim Analysis," Poster Presented At The European Respiratory Society International Congress; Sep. 15-19, 2018; Paris, France, 1 page.
Sitbon et al., "Selexipag for the Treatment of Pulmonary Arterial Hypertension", The New England Journal of Medicine, Dec. 24, 2015, vol. 373, No. 26, pp. 2522-2533.

* cited by examiner

TRANSITIONING PATIENTS TREATED FOR PULMONARY ARTERIAL HYPERTENSION TO SELEXIPAG

CROSS-REFERENCE TO RELATED APPLICATIONS

This application is the National Stage Application of International Patent Application No. PCT/EP2020/064089, filed May 20, 2020, which claims priority to U.S. Provisional Patent Application No. 62/850,792, filed May 21, 2019, the disclosures of which are incorporated by reference herein.

FIELD OF THE INVENTION

This invention relates to methods for transitioning a patient being treated for pulmonary arterial hypertension to selexipag.

BACKGROUND

Pulmonary arterial hypertension (PAH) is a form of the broader condition pulmonary hypertension in which a patient has high blood pressure in the lungs. However, in PAH, the increased blood pressure is caused by obstruction in the lung's small arteries. Often, the cause of PAH is unknown. However, some causes of PAH include drug use, HIV-infection, connective tissue diseases, autoimmune disorders, to name a few. Regardless of the cause, PAH typically leads to heart damage and, often, death when untreated.

The current treatment of PAH often, initially involves PAH-specific medications initially. However, the treatment is based on the patient and the severity of the symptoms, among other factors. In some patients, the disease progresses in spite of treatment, leading to lung transplantation as the only treatment option.

What is needed are alternate treatments of PAH.

SUMMARY OF THE INVENTION

In some aspects, the disclosure provides methods of transitioning a patient being treated for pulmonary arterial hypertension with a non-selexipag prostacyclin pathway agent (PPA) to selexipag. The methods include administering selexipag to the patient at a starting dose and increasing to a highest tolerable maintenance dose that is maintained for greater than about 14 days without change or interruption. In some embodiments, the patient was taking the non-selexipag PPA for about 30 or more days at the time of selexipag initiation and stopped the non-selexipag PPA less than about 7 days before the selexipag initiation. In other embodiments, the patient continued taking the non-selexipag PPA at the time of selexipag initiation and subsequently stopped the non-selexipag PPA.

DETAILED DESCRIPTION OF ILLUSTRATIVE EMBODIMENTS

Figure 1A:
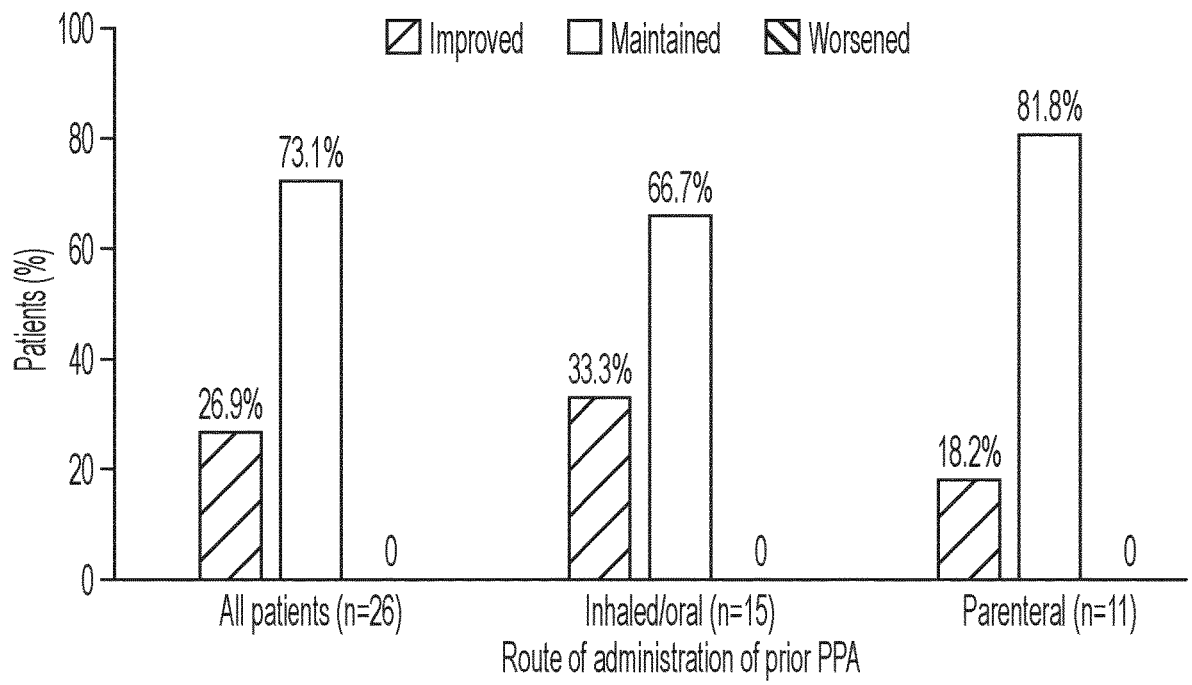
FIG. 1A is a bar graph showing the change in WHO functional class from baseline to 6 months.

In the present disclosure the singular forms "a", "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiments and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Methods

The present disclosure provides methods of transitioning a patient being treated for pulmonary arterial hypertension with a non-selexipag prostacyclin pathway agent (PPA) to selexipag. The terms "pulmonary arterial hypertension" and "PAH" are interchangeable and define a condition of pulmonary hypertension where the patient has high blood pressure in the lungs. PAH occurs when the very small arteries throughout the lungs narrow in diameter, which increases the resistance to blood flow through the lungs. In some embodiments, the underlying cause of the narrowing is not known, i.e., idiopathic pulmonary hypertension. PAH also is classified into subgroups including (i) familial, or heritable PAH, (ii) PAH caused by drugs or toxins, (iii) PAH associated with other conditions such as connective tissue diseases (scleroderma or lupus), congenital heart problems, high blood pressure in the liver, HIV, infections (schistosomiasis), and sickle cell anemia, (iv) PAH caused by rare blood conditions (pulmonary veno-occlusive disease or pulmonary capillary hemangiomatosis, or (v) PAH in babies (persistent pulmonary hypertension of the newborn).

The methods described herein also may include a determination that the patient has PAH. Typically, that determination is made by an attending physician. A diagnosis or determination of PAH may be performed using techniques known by those of skill in the art. For example, a right-heart catheterization may be conducted to confirm pulmonary arterial hypertension in a patient.

In some embodiments, the methods described herein advantageously improve the patient's World Health Organization functional class after about 12 months following selexipag initiation. In other embodiments, the methods improve the patient's 6-minute walk distance after about 12 months following selexipag initiation. In further embodiments, the methods described herein advantageously improve the patient's World Health Organization functional class and 6-minute walk distance after about 12 months, following selexipag initiation.

Prior to initiating treatment with selexipag, the patient is typically in World Health Organization (WHO) functional class II, III, or IV. As known to those skilled in the art, the WHO classifies pulmonary hypertension into classes I-IV. See, Table A. In some embodiments, the patient is in WHO functional class II prior to treatment with selexipag. In other embodiments, the patient is in a WHO functional class III prior to treatment with selexipag. In further embodiments, the patient is in WHO functional class IV prior to treatment with selexipag.

have been taking the non-selexipag for at least about 30 days, about 60 days, about 90 days, about 180 days, about 210 days, about 240 days, about 270 days, about 300 days, about 330 days, about 360 days, about 1 year, about 2 years, about 3 years, about 4 years, or about 5 years.

The patient will have stopped taking the non-selexipag PPA upon initiating treatment with selexipag. In some embodiments, the patient will have stopped taking the non-selexipag less than about 7 days before the selexipag initiation. In other embodiments, the patient continued taking the non-selexipag PPA at the time of selexipag initiation and subsequently stopped the non-selexipag PPA. Thus, there may be some overlap in the dosing of selexipag and the non-selexipag PPA.

The term "non-selexipag prostacyclin pathway agent" or "non-selexipag PPA" as used herein refers to any pharmaceutical agent that acts as a prostatcyclin pathway agent, but is not selexipag or its metabolite, as defined herein. The non-selexipag PPA may be an inhaled PPA, an oral PPA, or a parenteral PPA. In some embodiments, the non-selexipag PPA is an inhaled or oral PPA. In other embodiments, the non-selexipag PPA is an inhaled PPA. In further embodiments, the non-selexipag PPA is an oral PPA. In further embodiments, the non-selexipag PPA is a parenteral PPA such as a subcutaneous or intravenous PPA. In some aspects, the non-selexipag parenteral PPA is a subcutaneous PPA. In other aspects, the non-selexipag parenteral PPA is an intravenous PPA. Non-limiting examples of non-selexipag PPAs include epoprostenol (Flolan®, Veletri®), treprostinil (Remodulin®, Tyvaso®, Orenitram®), or iloprost (Ilomedin™ Ventavis®). In some embodiments, the non-selexipag PPA is intravenous epoprostenol, treprostinil, or iloprost. In other embodiments, the non-selexipag PPA is subcutaneous treprostinil. In further embodiments, the non-selexipag PPA is inhaled treprotinil or iloprost. In still other embodiments, the non-selexipag PPA is oral treprostinil.

The methods comprise administering a starting dose of selexipag to the patient and increasing it to a highest tolerable maintenance dose that is maintained for greater than about 14 days without change or interruption.

The selexipag is administered at a starting dose and is increased to determine a maintenance dose. The term "maintenance dose" as used herein refers to the amount of selexipag that may be administered to a patient per day, without resulting in adverse physical and/or pharmacological effects.

TABLE A

WHO Functional Classification of Pulmonary Hypertension

| | |
|---|---|
| Class I | Patients with pulmonary hypertension but without resulting limitation of physical activity. Ordinary physical activity does not cause undue dyspnea or fatigue, chest pain or near syncope. |
| Class II | Patients with pulmonary hypertension resulting in slight limitation of physical activity. They are comfortable at rest. Ordinary physical activity causes undue dyspnea or fatigue, chest pain or near syncope. |
| Class III | Patients with pulmonary hypertension resulting in marked limitation of physical activity. They are comfortable at rest. Less than ordinary activity causes undue dyspnea or fatigue, chest pain or near syncope. |
| Class IV | Patients with pulmonary hypertension with inability to carry out any physical activity without symptoms. These patients manifest signs of right heart failure. Dyspnea and/or fatigue may even be present at rest. Discomfort is increased by any physical activity. |

Prior to initiating treatment with selexipag, the patient will have been taking the non-selexipag PPA. In some embodiments, the patient will have been taking the non-selexipag PPA for about 30 days or more at the time of selexipag initiation. In other embodiments, the patient will Thus, the maintenance dose is typically evaluated for each patient on an individual basis. In some aspects, the starting dose of selexipag is the same as the maintenance dose. In further aspects, the starting dose of selexipag is lower than the maintenance dose.

The starting dose or the maintenance dose, on a daily basis, is at least about 10 µg. In some embodiments, the starting dose or the maintenance dose, on a daily basis, is at least about 100, about 200, about 300, about 400, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, or about 3500 µg. In some embodiments, the starting dose is about 200 twice daily. The daily dose may be administered once daily, twice daily, or thrice daily, preferably twice daily.

Desirably, the maintenance dose not exceed about 1600 µg twice daily, i.e., 3200 µg per day. In some embodiments, the maintenance dose, twice daily, is about 100 to about 3500 about 200 to about 3200, about 200 to about 3000, about 200 to about 2800, about 200 to about 2600, about 200 to about 2400, about 200 to about 2200, about 200 to about 2000, about 200 to about 1800, about 200 to about 1600, about 200 to about 1400, about 200 to about 1200, about 200 to about 1000, about 200 to about 800, about 200 to about 600, about 200 to about 400, about 400 to about 3200, about 400 to about 3000, about 400 to about 2800, about 400 to about 2600, about 400 to about 2400, about 400 to about 2200, about 400 to about 2000, about 400 to about 1800, about 400 to about 1600, about 400 to about 1400, about 400 to about 1200, about 400 to about 1000, about 400 to about 800, about 400 to about 600, about 600 to about 3200, about 600 to about 3000, about 600 to about 2800, about 600 to about 2600, about 600 to about 2400, about 600 to about 2200, about 600 to about 2000, about 600 to about 1800, about 600 to about 1600, about 600 to about 1400, about 600 to about 1200, about 600 to about 1000, about 600 to about 800, about 800 to about 3200, about 800 to about 3000, about 800 to about 2800, about 800 to about 2600, about 800 to about 2400, about 800 to about 2200, about 800 to about 2000, about 800 to about 1800, about 800 to about 1600, about 800 to about 1400, about 800 to about 1200, about 800 to about 1000, about 1000 to about 3200, about 1000 to about 3000, about 1000 to about 2800, about 1000 to about 2600, about 1000 to about 2400, about 1000 to about 2200, about 1000 to about 2000, about 1000 to about 1800, about 1000 to about 1600, about 1000 to about 1400, about 1000 to about 1200, about 1200 to about 3200, about 1200 to about 3000, about 1200 to about 2800, about 1200 to about 2600, about 1200 to about 2400, about 1200 to about 2200, about 1200 to about 2000, about 1200 to about 1800, about 1200 to about 1600, about 1200 to about 1400, about 1400 to about 3200, about 1400 to about 3000, about 1400 to about 2800, about 1400 to about 2600, about 1400 to about 2400, about 1400 to about 2200, about 1400 to about 2000, about 1400 to about 1800, about 1400 to about 1600, about 1600 to about 3200, about 1600 to about 3000, about 1600 to about 2800, about 1600 to about 2600, about 1600 to about 2400, about 1600 to about 2200, about 1600 to about 2000, about 1600 to about 1800, about 1800 to about 3200, about 1800 to about 3000, about 1800 to about 2800, about 1800 to about 2600, about 1800 to about 2400, about 1800 to about 2200, about 1800 to about 2000, about 2000 to about 3200, about 2000 to about 3000, about 2000 to about 2800, about 2000 to about 2600, about 2000 to about 2400, about 2000 to about 2200, about 2200 to about 3200, about 2200 to about 3000, about 2200 to about 2800, about 2200 to about 2600, about 2200 to about 2400, about 2400 to about 3200, about 2400 to about 3000, about 2400 to about 2800, about 2400 to about 2600, about 2600 to about 3200, about 2600 to about 3000, about 2600 to about 2800, about 2800 to about 3200, about 2800 to about 3000, or about 3000 to about 3200 µg. In further embodiments, the maintenance dose, on a twice daily basis, is about 200 to about 1600 µg. In other embodiments, the maintenance dose is about 1000 µg to about 1600 µg twice daily. In yet further embodiments, the maintenance dose, on a twice daily basis, is about 1400 to about 1600 µg.

Desirably, the starting dose is increased until the maintenance dose is reached. This period of increasing the dose may be determined by one skilled in the art. Typically, the time to reach the maintenance dose is at least about 1 week. In some embodiments, the time to reach the maintenance dose is at least about 2, about 3, about 4, about 5, about 6, about 7, about 8, about 9, about 10, about 11, about 12, about 13, about 14, about 15, or about 16 weeks. In other embodiments, the time to reach the maintenance dose is about 2 to about 16 weeks, about 2 to about 14 weeks, about 2 to about 12 weeks, about 2 to about 10, weeks, about 2 to about 8 weeks, about 2 to about 6 weeks, about 2 to about 4 weeks, about 4 to about 16 weeks, about 4 to about 14 weeks, about 4 to about 12 weeks, about 4 to about 10 weeks, about 4 to about 8 weeks, about 4 to about 6 weeks, about 5 to about 15 weeks, about 5 to about 10 weeks, about 6 to about 16 weeks, about 6 to about 14 weeks, about 6 to about 12 weeks, about 6 to about 10 weeks, about 6 to about 8 weeks, about 8 to about 16 weeks, about 8 to about 14 weeks, about 8 to about 12 weeks, about 8 to about 10 weeks, about 10 to about 16 weeks, about 12 to about 16 weeks, about 12 to about 14 weeks, or about 14 weeks to about 16 weeks. In further embodiments, the time to reach the maintenance dose is about 5 to about 10 weeks.

During the time to reach the maintenance dose, the selexipag dose is increased as determined by one skilled in the art until the maintenance dose is determined. In some embodiments, the selexipag dose is increased daily. In other embodiments, the selexipag dose is increased weekly. In further embodiments, the selexipag dose is increased monthly. Preferably, the selexipag dose is increased weekly (based on a 7-day week). When increased weekly, the selexipag dose may be administered on the same day each week or within 1 day within the scheduled dosing day. For example, if the selexipag dose in administered on a Monday, the next dose of selexipag may be administered on Sunday, Monday, or Tuesday of the following week. When increased monthly, the selexipag dose may be administered of the same day each month or within 3 days of the next scheduled dosing day. For example, if the selexipag dose in administered on January $7^{th}$, the next dose of selexipag may be administered on February $4^{th}$, $5^{th}$, $6^{th}$, $7^{th}$, $8^{th}$, $9^{th}$, or $10^{th}$.

Once the maintenance dose is reached, it is maintained during a maintenance phase. The length of this maintenance phase may be determined by one skilled in the art and is, typically, at least about 14 weeks, and may continue as long as the patient is in need of therapy. In some embodiments, the maintenance phase is about 14, about 16, about 18, about 20, about 22, about 24, about 26, about 28, about 30, about 32, about 34, about 36, about 38, about 40, about 42, about 44, about 46, about 48, about 50, or about 52 weeks. In other embodiments, the maintenance phase is at least about 14 weeks. In further embodiments, the maintenance phase is at least about 26 weeks.

Additional dose increases may occur following the maintenance phase as determined by those skilled in the art. However, any such increases desirably do not exceed 1600 µg twice daily.

The methods include administering a therapeutically effective amount of the selexipag. The term "therapeutically effective amount" as used herein, means that amount of active compound or pharmaceutical agent that elicits the biological or medicinal response in a human that is being sought by a researcher, medical doctor, or other clinician, which includes alleviation of the symptoms of the disease or disorder being treated. The selexipag may be administered once daily, twice daily, or thrice daily to achieve the therapeutically effective amount. In some aspects, the selexipag is administered once daily. In other aspects, the selexipag is administered twice daily. In further aspects, the selexipag is administered thrice daily. Preferably, the selexipag is administered twice daily to achieve the therapeutically effective amount.

As used herein, unless otherwise noted, the term "selexipag" refers to 2-{4-[(5,6-diphenylpyrazin-2-yl)(propan-2-yl)amino]butoxy}-N-(methanesulfonyl)acetamide of formula (I).

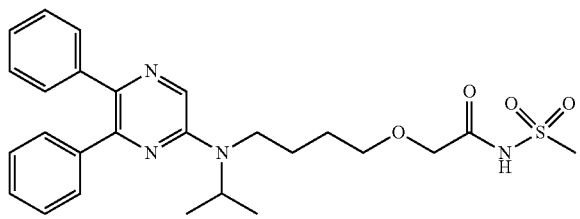

I

As used herein, "selexipag" also refers to amorphous or crystalline forms of selexipag, such as polymorphs thereof. In some embodiments, the selexipag is a crystalline form, such as a polymorph. In other embodiments, the selexipag is an amorphous form. In other embodiments, the selexipag is the Form I as described in U.S. Pat. Nos. 8,791,122 and 9,284,280, Form II as described in U.S. Pat. No. 9,340,516, or Form III as described in U.S. Pat. No. 9,440,931, all of which are incorporated by reference herein. The crystallinity may be determined by those skilled in the art using one or more techniques such as, e.g., single crystal x-ray diffraction, powder x-ray diffraction, differential scanning calorimetry, melting point, among others.

"Selexipag" as used herein includes anhydrous or hydrates thereof. In certain embodiments, the selexipag is an anhydrous form. In other embodiments, the selexipag is a hydrate thereof.

"Selexipag" as used herein further refers to solvates thereof. Such solvates include a molecule of a solvent bound through intermolecular forces or chemical bonds to one or more locations of the selexipag molecule.

The term "selexipag" may also include pharmaceutically acceptable salts thereof, which may readily be selected by those skilled in the art. A "pharmaceutically acceptable salt" is intended to mean a salt of selexipag that is non-toxic, biologically tolerable, or otherwise biologically suitable for administration to the subject. See, e.g., Berge, "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002, which are incorporated herein by reference. Selexipag can be used in the form of a free base or acid, but can also be used after forming into a pharmaceutically acceptable salt by a known method. When the selexipag is basic, examples of "salt" include salts of inorganic acids such as hydrochloric acid, sulfuric acid, nitric acid, phosphoric acid, hydrofluoric acid and hydrobromic acid, and salts of organic acids such as acetic acid, tartaric acid, lactic acid, citric acid, fumaric acid, maleic acid, succinic acid, methanesulfonic acid, ethanesulfonic acid, benzenesulfonic acid, p-toluenesulfonic acid, naphthalenesulfonic acid and camphorsulfonic acid. When the selexipag is acidic, examples of "salt" include alkali metal salts such as sodium salt and potassium salt, and alkali earth metal salts such as calcium salt.

Geometrical isomers (Z form and E form) of selexipag or mixtures thereof are also contemplated.

Selexipag is commercially available as understood to those skilled in the art. See, e.g., U.S. Pat. No. 7,205,302, which is incorporated by reference herein. For example, selexipag is available as Uptravi® and also is known as ACT-293987 or NS-304. Selexipag is an agonist of the prostacyclin receptor and may be prepared according to the process as disclosed in U.S. Pat. No. 7,205,302.

The present disclosure also contemplates the administration of selexipag metabolites. Desirably, the selexipag metabolite is metabolically active compound. Thus, in certain embodiments, the selexipag metabolite is of formula M1. M1 is also known under the code name ACT-333679 or MRE-269.

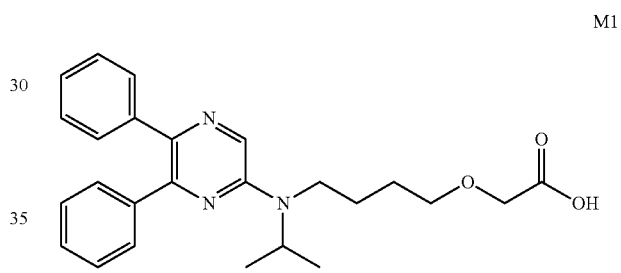

M1

As used herein, unless otherwise noted, the terms "treating", "treatment" and the like, shall include the management and care of a patient for the purpose of combating a disease, condition, or disorder. The terms "treating" and "treatment" also include the administration of the compounds or pharmaceutical compositions as described herein to (a) alleviate one or more symptoms or complications of the disease, condition or disorder; (b) prevent the onset of one or more symptoms or complications of the disease, condition or disorder; and/or (c) eliminate one or more symptoms or complications of the disease, condition, or disorder.

As used herein, unless otherwise noted, the terms "preventing", "prevention" and the like, shall include (a) reducing the frequency of one or more symptoms; (b) reducing the severity of one or more symptoms; (c) delaying, slowing or avoiding of the development of additional symptoms; and/or (d) slowing, or avoiding the development of the disorder or condition to a later stage or more serious form.

One skilled in the art will recognize that, wherein the present disclosure is directed to methods of prevention, a patient in need thereof shall include any patient or patient who has experienced or exhibited at least one symptom of the disorder, disease or condition to be prevented. Further, a patient in need thereof may additionally be a patient who has not exhibited any symptoms of the disorder, disease or condition to be prevented, but who has been deemed by a physician, clinician or other medical profession to be at risk of developing said disorder, disease or condition. For example, the patient may be deemed at risk of developing a disorder, disease or condition (and therefore in need of prevention or preventive treatment) as a consequence of the patient's medical history, including, but not limited to, family history, pre-disposition, co-existing (comorbid) disorders or conditions, genetic testing, and the like.

The terms "subject" and "patient" are interchangeably used herein to refer to a human, who has been the object of treatment, observation or experiment. Preferably, the patient has experienced and/or exhibited at least one symptom of the disease or disorder to be treated and/or prevented.

In the methods described herein, the therapeutically effective amount of selexipag is safe. As used herein, unless otherwise noted, the term "safe" shall mean without undue adverse side effects (such as toxicity, irritation, or allergic response), commensurate with a reasonable benefit/risk ratio when used in the manner of this invention.

Formulations/Compositions

Pharmaceutical compositions containing selexipag as the active ingredient can be prepared by intimately mixing the compound or compounds with a pharmaceutical carrier according to conventional pharmaceutical compounding techniques. As used herein, the terms "composition" and "formulation" are used interchangeably and encompass a product comprising the specified ingredients in the specified amounts, as well as any product, such as a pharmaceutical product, which results, directly or indirectly, from combinations of the specified ingredients in the specified amounts. A summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Selexipag may be administered to a patient neat or in a mixture with a pharmaceutically acceptable non-toxic inert carrier, for example, as a pharmaceutical composition containing the compound at a level of 0.1% to 99.5 wt %, preferably 0.5% to 90%, based on the total weight of the composition. As a carrier, one or more of auxiliary agents for formulations such as solid, semi-solid and liquid diluent, filler and other auxiliary agents for drug formulations may be used. It is desirable that a pharmaceutical composition is administered as a unit dosage form. The pharmaceutical composition can be administered into tissue, or intravenously, orally, topically (percutaneously) or rectally. It is a matter of course that a dosage form suitable for any of the administration modes described above is employed. For example, oral administration is preferable.

The pharmaceutical compositions may be administered by a number of routes as determined by those skilled in the art. Preferably, the pharmaceutical compositions are administered by route that is suitable for selexipag. In some embodiments, the pharmaceutical compositions are administered orally, parenterally, or any combination thereof. In other embodiments, the pharmaceutical compositions are administered orally. In further embodiments, the pharmaceutical compositions are administered parenterally.

The pharmaceutical compositions may administered in a form suitable for the selected route of administration. Thus, the pharmaceutical compositions may be administered as suspensions, elixirs, solutions, powders, pills such as capsules, tablets, or caplets, pastilles, granules, syrups, thin films, lozenges, sprays, pastes, or injections. In some embodiments, the pharmaceutical compositions are administered as injections such as intradermal injections, subcutaneous injections, intramuscular injections, intraosseous injections, intraperitoneal injections, or intravenous injections. In other embodiments, the pharmaceutical compositions are administered as suspensions, elixirs, solutions, powders, pills such as capsules (hard or soft), tablets, or caplets, pastilles, granules, syrups, thin films, lozenges, sprays, or pastes. In further embodiments, the pharmaceutical compositions are administered via a continuous infusion via a central venous catheter, using, e.g., an ambulatory pump or implantable pump. In still other embodiments, the pharmaceutical compositions are administered via continuous infusion using a subcutaneous catheter.

The pills may be formulated for swallowing, chewable, sublingual use, or buccal use, or may be effervescent to be dissolved or dispersed in water prior to administration. In some embodiments, the pharmaceutical product comprises a pill, tablet, powder, sterile parenteral solution, or liquid spray. Desirably, the pharmaceutical product comprises a tablet.

The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Thus, for parenteral administration, the pharmaceutical composition or pharmaceutical product is a sterile, parenteral solution. Injectable suspensions or solutions may also be prepared utilizing aqueous carriers along with appropriate additives.

To prepare such pharmaceutical compositions, selexipag, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutical compositions herein will contain, per unit dosage unit, e.g., tablet, capsule, powder, injection, suppository, teaspoonful and the like, preferably a tablet, of at least about 100, about 200, about 300, about 400, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, or about 3500 µg. In some embodiments, the pharmaceutical composition comprises about 100 to about 3500 about 200 to about 3200, about 200 to about 3000, about 200 to about 2800, about 200 to about 2600, about 200 to about 2400, about 200 to about 2200, about 200 to about 2000, about 200 to about 1800, about 200 to about 1600, about 200 to about 1400, about 200 to about 1200, about 200 to about 1000, about 200 to about 800, about 200 to about 600, about 200 to about 400, about 400 to about 3200, about 400 to about 3000, about 400 to about 2800, about 400 to about 2600, about 400 to about 2400, about 400 to about 2200, about 400 to about 2000, about 400 to about 1800, about 400 to about 1600, about 400 to about 1400, about 400 to about 1200, about 400 to about 1000, about 400 to about 800, about 400 to about 600, about 600 to about 3200, about 600 to about 3000, about 600 to about 2800, about 600 to about 2600, about 600 to about 2400, about 600 to about 2200, about 600 to about 2000, about 600 to about 1800, about 600 to about 1600, about 600 to about 1400, about 600 to about 1200, about 600 to about 1000, about 600 to about 800, about 800 to about 3200, about 800 to about 3000, about 800 to about 2800, about 800 to about 2600, about 800 to about 2400, about 800 to about 2200, about 800 to about 2000, about 800 to about 1800, about 800 to about 1600, about 800 to about 1400, about 800 to about 1200, about 800 to about 1000, about 1000 to about 3200, about 1000 to about 3000, about 1000 to about 2800, about 1000 to about 2600, about 1000 to about 2400, about 1000 to about 2200, about 1000 to about 2000, about 1000 to about 1800, about 1000 to about 1600, about 1000 to about 1400, about 1000 to about 1200, about 1200 to about 3200, about 1200 to about 3000, about 1200 to about 2800, about 1200 to about 2600, about 1200 to about 2400, about 1200 to about 2200, about 1200 to about 2000, about 1200 to about 1800, about 1200 to about 1600, about 1200 to about 1400, about 1400 to about 3200, about 1400 to about 3000, about 1400 to about 2800, about 1400 to about 2600, about 1400 to about 2400, about 1400 to about 2200, about 1400 to about 2000, about 1400 to about 1800, about 1400 to about 1600, about 1600 to about 3200, about 1600 to about 3000, about 1600 to about 2800, about 1600 to about 2600, about 1600 to about 2400, about 1600 to about 2200, about 1600 to about 2000, about 1600 to about 1800, about 1800 to about 3200, about 1800 to about 3000, about 1800 to about 2800, about 1800 to about 2600, about 1800 to about 2400, about 1800 to about 2200, about 1800 to about 2000, about 2000 to about 3200, about 2000 to about 3000, about 2000 to about 2800, about 2000 to about 2600, about 2000 to about 2400, about 2000 to about 2200, about 2200 to about 3200, about 2200 to about 3000, about 2200 to about 2800, about 2200 to about 2600, about 2200 to about 2400, about 2400 to about 3200, about 2400 to about 3000, about 2400 to about 2800, about 2400 to about 2600, about 2600 to about 3200, about 2600 to about 3000, about 2600 to about 2800, about 2800 to about 3200, about 2800 to about 3000, or about 3000 to about 3200 µg of selexipag. In further embodiments, the pharmaceutical composition comprises about 200 to about 1600 µg of selexipag. In yet other embodiments, the pharmaceutical composition comprises about 200 µg of selexipag. In still further embodiments, the pharmaceutical composition comprises about 400 µg of selexipag. In other embodiments, the pharmaceutical composition comprises about 800 µg of selexipag. In further embodiments, the pharmaceutical composition comprises about 1000 µg of selexipag. In still other embodiments, the pharmaceutical composition comprises about 1200 µg of selexipag. In yet further embodiments, the pharmaceutical composition comprises about 1400 µg of selexipag. In other embodiments, the pharmaceutical composition comprises about 1600 µg of selexipag. The dosages, however, may be varied depending upon the requirement of the patients, the severity of the condition being treated and the compound being employed.

Preferably the pharmaceutical compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. For preparing solid compositions such as tablets, the principal active ingredient (e.g., selexipag) is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a pharmaceutically acceptable salt thereof. In certain embodiments, two active ingredients can be formulated together, e.g., in a bi-layer tablet formulation. When referring to these preformulation compositions as homogeneous, it is meant that the active ingredients are dispersed evenly throughout the composition so that the composition may be readily subdivided into equally effective dosage forms such as tablets, pills and capsules. The tablets or pills of the composition can be coated or otherwise compounded to provide a dosage form affording the advantage of prolonged action. For example, the tablet or pill can comprise an inner dosage and an outer dosage component, the latter being in the form of an envelope over the former.

The liquid forms in which the compositions of the present disclosure may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods described herein may also be carried out using a pharmaceutical composition comprising selexipag and a pharmaceutically acceptable carrier. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, selexipag may be administered in a single daily dose, or the total daily dosage may be administered in divided doses of two, three or four times daily.

For instance, for oral administration in the form of a tablet or capsule, the active drug component (e.g., selexipag) can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare pharmaceutical compositions of the present disclosure, selexipag, as the active ingredient, may be intimately admixed with a pharmaceutical carrier according to conventional pharmaceutical compounding techniques, which carrier may take a wide variety of forms depending of the form of preparation desired for administration (e.g., oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain, the disclosure of which is hereby incorporated by reference.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc., the disclosures of which are hereby incorporated by reference.

Abbreviations: IQR=interquartile range; PAH=pulmonary arterial hypertension; CH=pulmonary capillary hemangiomatosis; PPA=prostacyclin pathway agent; PVOD=pulmonary veno-occlusive disease; mPAP=mean pulmonary arterial pressure; YHA=New York Heart Association; PCWP=pulmonary capillary wedge pressure; PVR=pulmonary vascular resistance; RAP=right atrial pressure; WHO=World Health Organization; AE=adverse event.

EXAMPLE

Example 1

Selexipag is supplied as round, film-coated tablets in different strengths: 200, 400, 600, 800, 1000, 1200, 1400, and 1600 µg strength.

The compositions are given in Table A and Table B.

TABLE A

Composition of selexipag film-coated tablets (200-800 µg)

| Ingredients | Selexipag film-coated tablet | | | |
|---|---|---|---|---|
| | 200 µg | 400 µg | 600 µg | 800 µg |
| | Amount (mg) | | | |
| Selexipag | 0.2 | 0.4 | 0.6 | 0.8 |
| Mannitol | 72.6 | 72.4 | 72.2 | 72.0 |
| Maize starch | | 48.0 | | |
| Low substituted hydroxypropylcellulose | | 6.8 | | |
| Hydroxypropylcellulose | | 5.4 | | |
| Magnesium stearate | | 2.0 | | |
| Core tablet weight | | 135.0 | | |
| Hypromellose | | 3.8000 | | |
| Propylenglycol | | 0.7000 | | |
| Titanium dioxide | 0.4505 | 0.3500 | 0.4880 | 0.1500 |
| Iron oxide red | — | 0.1500 | 0.0050 | — |
| Iron oxide black | — | — | 0.0070 | 0.1000 |
| Iron oxide yellow | 0.0495 | — | — | 0.2500 |
| Carnauba wax | | 0.040 | | |
| Coating weight | | 5.0 | | |
| Total weight of film-coated tablet | | 140.0 mg | | |

TABLE B

Composition of selexipag film-coated tablets (1000-1600 µg)

| Ingredients | Selexipag film-coated tablet | | | |
|---|---|---|---|---|
| | 1000 µg | 1200 µg | 1400 µg | 1600 µg |
| | Amount (mg) | | | |
| Selexipag | 1.0 | 1.2 | 1.4 | 1.6 |
| Mannitol | 71.8 | 71.6 | 71.4 | 71.2 |
| Maize starch | | 48.0 | | |
| Low substituted hydroxypropylcellulose | | 6.8 | | |
| Hydroxypropylcellulose | | 5.4 | | |
| Magnesium stearate | | 2.0 | | |
| Core tablet weight | | 135.0 | | |
| Hypromellose | | 3.8000 | | |
| Propylenglycol | | 0.7000 | | |
| Titanium dioxide | 0.4310 | 0.4640 | 0.2500 | 0.1500 |
| Iron oxide red | 0.0195 | 0.0150 | — | 0.1250 |
| Iron oxide black | — | 0.0210 mg | — | 0.1250 |
| Iron oxide yellow | 0.0495 | — | 0.2500 | 0.1000 |
| Carnauba wax | | 0.040 | | |
| Coating weight | | 5.0 | | |
| Total weight of film-coated tablet | | 140.0 mg | | |

Example 2

In this example, the effectiveness of transitioning patients from a non-selexipag PPA to selexipag was investigated. Patients were followed for up to 18 months and data were collected at the time of initiation, enrollment, and approximately quarterly post-enrollment. Eligible patients were aged ≥18 years and either newly initiated on selexipag at the time of enrollment or were already receiving selexipag and have a documented titration regimen. This data was obtained from a subgroup of the first 250 patients who had transitioned from another PPA.

"Transitioned patients" were defined as patients who were (i) taking a non-selexipag PPA for ≥30 days at the time of selexipag initiation who stopped the initial agent ≤7 days before selexipag initiation; or (ii) continued taking the initial, non-selexipag PPA when they initiated selexipag and gradually transitioned off that agent.

The maintenance dose was defined as the first dose post-titration maintained for ≥14 days without change and/or interruption. The patient data collected included (i) demographics, medical history, disease characteristics, and background therapy; (ii) the transition process from non-selexipag PAH treatments to selexipag and from selexipag to non-selexipag PPAs; (iii) the selexipag dosing regimen; (iv) clinical course and outcomes; and (v) adverse events.

Assessments performed closest to selexipag initiation were considered to be "baseline." Data at 6 and 12 months post-baseline were as follows (i) the window for the 6-month measurements was >0 months and <9 months; (ii) the window for the 12-month measurements was ≥9 months and <16 months; and (iii) the assessment closest to the 6- or 12-month time point, respectively, was used.

AEs known to be associated with the selexipag mechanism of action were only reported if they were serious, led to selexipag discontinuation, or reflected an unusual pattern of severity.

A. Risk Category Determination

Risk categories were assigned. Seven variables were used: World Health Organization or New York Heart Association functional class (FC), 6-minute walk distance (6MWD), N-terminal prohormone of brain natriuretic peptide (NT-proBNP), brain natriuretic peptide (BNP), and hemodynamic parameters, including right atrial pressure, cardiac index, and mixed venous oxygen saturation. If both NT-proBNP and BNP were available, the risk classification of each value was averaged together and the mean was used in the risk categorization. Thresholds from the 2015 European Society of Cardiology/European Respiratory Society Guidelines were applied to assign a risk score for each available variable: 1=low risk, 2=intermediate risk, and 3=high risk. The risk score from all available variables was then averaged. The resulting number was rounded to the nearest integer to produce the patient's individual risk category: 1=low risk, 2=intermediate risk, and 3=high risk B. Patients and Disease Characteristics Of the 250 patients, 56 (22.4%) were transitioned from a non-selexipag PPA and 194 (77.6%) were non-transitioned. Transitioned and non-transitioned patients had similar baseline characteristics, except transitioned patients were younger at the time of diagnosis (median, 52 years [IQR: 38.5-62.0 years] vs 57 years [IQR: 43.0-65.0 years]); had a longer median time from PAH diagnosis to selexipag initiation (5.6 [IQR 2.0-10.0] vs 3.1 [IQR: 1.2-6.9] years); were more likely to have idiopathic PAH (64% vs 49%); and had lower PVR (median 4.8 [IQR 3.6-7.0] vs 7.2 [IQR 4.6-9.8] Wood units) at the time of selexipag initiation. Transitioned patients had higher maintenance doses than non-transitioned patients (median dose, 1400 [IQR 1000-1600] vs 1200 [IQR 800-1600] µg twice a day [BID])

Of the 56 transitioned patients, 8 transitioned from an oral, non-selexipag PPA, 28 transitioned from an inhaled, non-selexipag PPA, 3 transitioned from a non-selexipag PPA administered subcutaneously (SC), and 17 transitioned from a non-selexipag PPA administered intravenously (IV). Twenty-one (37.5%) patients transitioned to selexipag over 30 or fewer days, 16 (28.6%) transitioned over 31-60 days, and 19 (33.9%) transitioned over 60 or more days. In the latter group, eight patients transitioned from an inhaled non-selexipag PPA, three from an oral, non-selexipag PPA, six from an IV, non-selexipag PPA, and two from an SC, non-selexipag PPA.

In total, 16 of 56 transitioned patients (28.6%) discontinued selexipag compared with 65 of 194 (33.5%) non-transitioned patients. Selected patient demographics and disease characteristics for the 56 transitioned patients are shown in Table 1; disease severity data are shown in Table 2. Patient demographics were generally similar between patients who transitioned from parenteral, non-selexipag PPAs vs oral/inhaled, non-selexipag PPAs, although patients who transitioned from parenteral, non-selexipag PPAs were younger; had a shorter time from diagnosis to selexipag initiation; and had a shorter time from selexipag initiation to study enrollment. Median 6MWD, FC distribution, and hemodynamic data suggest that patients who transitioned from parenteral PPAs were in better health than those who transitioned from oral/inhaled, non-selexipag PPAs.

TABLE 1

Demographic and clinical characteristics at selexipag initiation in transitioned patients by route of administration of prior non-selexipag PPA

| Characteristics | All Transitioned Patients (N = 56) | Inhaled/Oral (n = 36) | Parenteral (n = 20) |
|---|---|---|---|
| Age at diagnosis, y | | | |
| Median (IQR) | 52.0 (38.5-62.0) | 56.0 (43.5-63.5) | 42.5 (32.5-59.0) |
| Age at time of Initiation, y | | | |
| Median (IQR) | 59.0 (46.5-68.5) | 61.0 (53.5-69.5) | 50.5 (37.5-66.0) |
| Sex, female, n (%) | 46 (82.1) | 29 (80.6) | 17 (85.0) |
| Race, n (%) | | | |
| White | 40 (71.4) | 27 (75.0) | 13 (65.0) |
| Black or African American | 11 (19.6) | 7 (19.4) | 4 (20.0) |
| Asian | 3 (5.4) | 1 (2.8) | 2 (10.0) |
| Hispanic | 2 (3.6) | 1 (2.8) | 1 (5.0) |

TABLE 1-continued

Demographic and clinical characteristics at selexipag initiation in transitioned patients by route of administration of prior non-selexipag PPA

| Characteristics | All Transitioned Patients (N = 56) | Inhaled/Oral (n = 36) | Parenteral (n = 20) |
|---|---|---|---|
| Etiology of PAH at diagnosis, n (%) | | | |
| Idiopathic | 36 (64.3) | 22 (61.1) | 14 (70.0) |
| Associated | 19 (33.9) | 14 (38.9) | 5 (25.0) |
| Connective Tissue Disease | 16 (28.6) | 11 (30.6) | 5 (25.0) |
| Congenital Heart Disease Portal | 2 (3.6) | 2 (5.6) | 0 (0.0) |
| Hypertension | 1 (1.8) | 1 (2.8) | 0 (0.0) |
| PVOD and/or PCH | 1 (1.8) | 0 (0.0) | 1 (5.0) |
| Time between diagnosis and selexipag treatment initiation, y | | | |
| Median (IQR) | 5.6 (2.0-10.0) | 6.3 (4.0-10.8) | 3.8 (1.6-9.5) |
| Duration of selexipag treatment between initiation and study enrollment, mo | | | |
| Median (IQR) | 7.8 (1.9-11.5) | 9.6 (3.7-11.5) | 2.1 (1.0-9.8) |
| Total duration of selexipag treatment, mo | | | |
| Median (IQR) | 19.7 (1.9-21.5) | 22.4 (14.9-27.6) | 16.6 (10.8-21.9) |

TABLE 2

Disease severity at selexipag initiation in transitioned patients by route of administration of prior non-selexipag PPA

| Characteristics | All Patients (N = 56) | Inhaled/Oral (n = 36) | Parenteral (n = 20) |
|---|---|---|---|
| NYHA/WHO functional class, n (%) | | | |
| I | 3 (5.4) | 2 (5.6) | 1 (5.0) |
| II | 16 (28.6) | 9 (25.0) | 7 (35.0) |
| III | 31 (55.4) | 21 (58.3) | 10 (50.0) |
| IV | 5 (8.9) | 3 (8.3) | 2 (10.0) |
| Unknown | 1 (1.8) | 1 (2.8) | 0 (0.0) |
| 6-Minute walk distance, n | 53 | 34 | 19 |
| Median (IQR), m | 299.0 (221.0-401.1) | 259.5 (192.0-345.0) | 347.5 (259.0-465.0) |
| Time since right heart catheterization, mo | | | |
| Median (IQR) | 13.3 (2.0-33.0) | 19.7 (4.7-49.6) | 4.5 (1.2-21.3) |
| mPAP at rest, n | 53 | 33 | 20 |
| Median (IQR), mmHg | 40.0 (31.0-50.0) | 45.0 (35.0-53.0) | 36.5 (27.0-45.0) |
| Mean RAP, n | 53 | 33 | 20 |
| Median (IQR), mmHg | 8.0 (5.0-12.0) | 9.0 (6.0-12.0) | 6.5 (4.5-11.0) |
| Mean PCWP at rest, n | 53 | 33 | 20 |
| Median (IQR), mmHg | 12.0 (9.0-15.0) | 13.0 (9.0-15.0) | 10.0 (6.0-14.0) |
| PVR, n | 51 | 31 | 20 |
| Median (IQR), Wood units | 4.8 (3.6-7.0) | 5.2 (3.7-7.0) | 4.2 (3.1-5.9) |

C. Selexipag Dosing

The median maintenance dose of selexipag in all transitioned patients was 1400 μg BID (IQR: 1000-1600 μg BID), and the median time to reach this dose was 8.1 weeks (IQR: 6.7-8.7 weeks). The median maintenance dose in patients who transitioned from a parenteral, non-selexipag PPA (1600 μg [IQR: 1400-1600 μg]) was higher than that in those who transitioned from an inhaled/oral, non-selexipag PPA (1300 μg [IQR: 1000-1600 μg]). The median time to reach these doses was 8.1 weeks in both groups (IQR: 5.6-8.4 weeks and 7.7-9.0 weeks in the inhaled/oral and parenteral groups, respectively).

D. Clinical Course

Figure 1B:
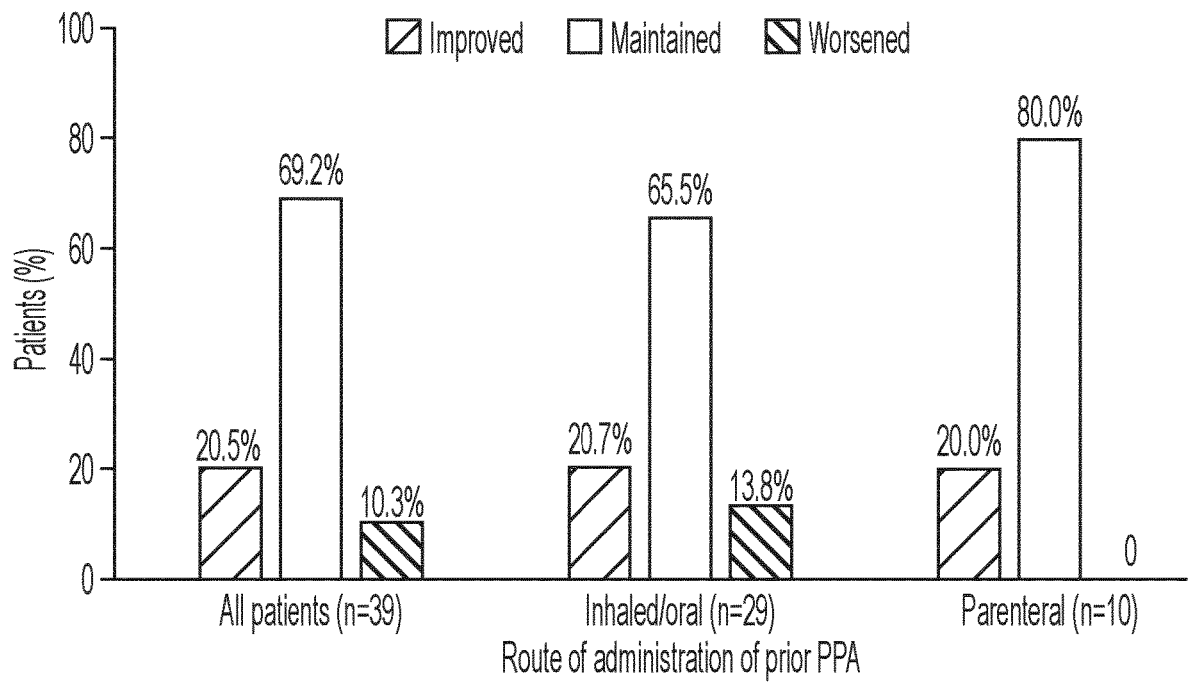
FIG. 1B is a bar graph showing the change in WHO functional class from baseline to 12 months by route of administration of prior PPA.

At 6 and 12 months, FC (FIGS. 1A and 1B) was maintained in the majority of transitioned patients. At 6 months, 27% had improved FC, and none had worsened FC. At 12 months, 21% had improved FC, and 10% had worsened FC. Data, however, were available for only 46% of patients at 6 months and 70% of patients at 12 months. FC results were generally similar between patients who had transitioned from an oral/inhaled, non-selexipag PPA or a parenteral, non-selexipag PPA.

Figure 2:
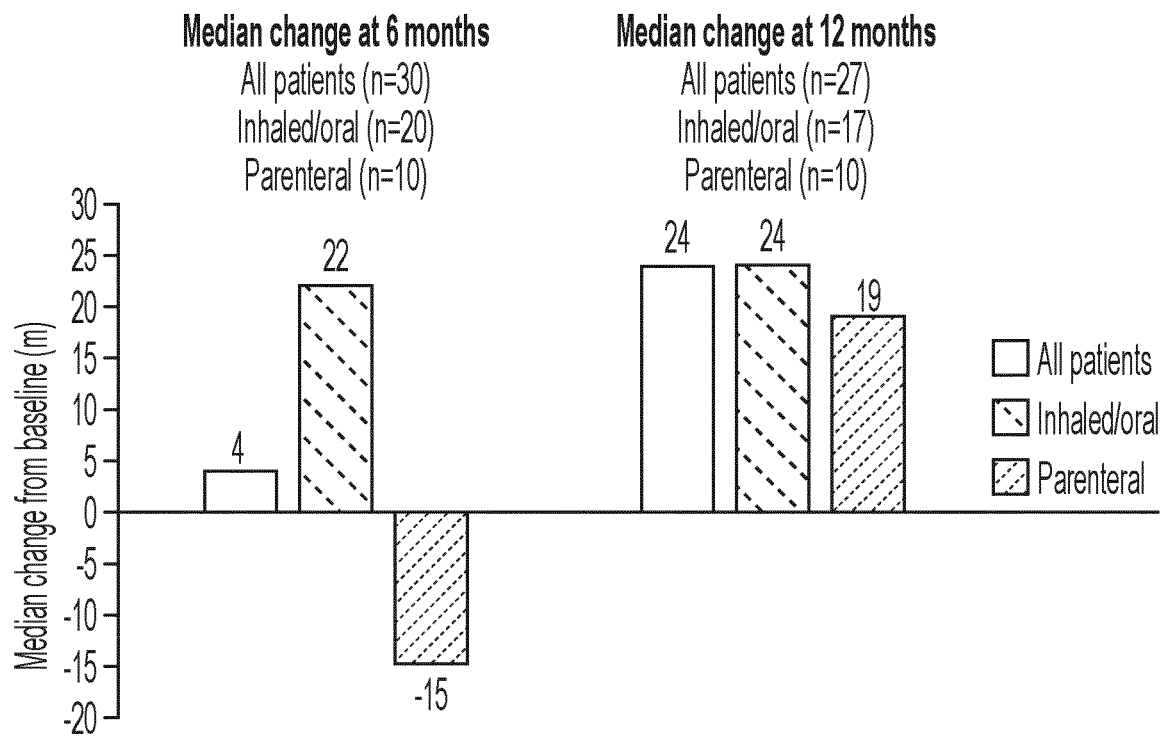
FIG. 2 is a bar graph showing the change from baseline in median 6-minute walk distance at 6 months and 12 months by route of administration of prior prostacyclin pathway agent.

At 6 months, 6MWD was similar to baseline in the overall transitioned population. However, patients who had transitioned from a parenteral, non-selexipag PPA had decreased median 6MWD from baseline, and those who transitioned from an oral/inhaled PPA had an increased 6MWD (FIG. 2).

By 12 months, all patients demonstrated a modest increase in 6MWD. Data were available for only 57% of patients at 6 months and for 52% of patients at 12 months.

sion (n=3); all of these patients had been transitioned from a parenteral, non-selexipag PPA (Table 3). Of note, one patient who had transitioned from a parenteral, non-selexipag PPA discontinued because of an increase in right ventricular systolic pressure.

TABLE 3

Adverse events leading to selexipag discontinuation in patients transitioned from inhaled/oral and parenteral non-selexipag PPAs

| Body System/Preferred Term | All Patients (N = 56) | Inhaled/Oral (n = 36) | Parenteral (n = 20) |
|---|---|---|---|
| Patients with at least one AE, n (%) | 11 (19.6) | 6 (16.7) | 5 (25.0) |
| Respiratory, thoracic and mediastinal disorders, n (%) | 5 (8.9) | 2 (5.6) | 3 (15.0) |
| Worsening pulmonary hypertension | 3 (5.4) | 0 | 3 (15.0) |
| Acute respiratory failure | 1 (1.8) | 1 (2.8) | 0 |
| Respiratory failure | 1 (1.8) | 1 (2.8) | 0 |
| Cardiac disorders, n (%) | 4 (7.1) | 2 (5.6) | 2 (10.0) |
| Cardiac arrest | 1 (1.8) | 1 (2.8) | 0 |
| Cardiac failure congestive | 1 (1.8) | 1 (2.8) | 0 |
| Fluid overload | 1 (1.8) | 0 | 1 (5.0) |
| Right ventricular failure | 1 (1.8) | 0 | 1 (5.0) |
| Investigations, n (%) | | | |
| Right ventricular systolic pressure | 1 (1.8) | 0 | 1 (5.0) |
| increased | 1 (1.8) | 0 | 1 (5.0) |
| Musculoskeletal and connective tissue disorders, n (%) | 1 (1.8) | 1 (2.8) | 0 |
| Arthralgia | 1 (1.8) | 1 (2.8) | 0 |
| Nervous system disorders, n (%) | 1 (1.8) | 1 (2.8) | 0 |
| Headache | 1 (1.8) | 1 (2.8) | 0 |

Figure 3A:
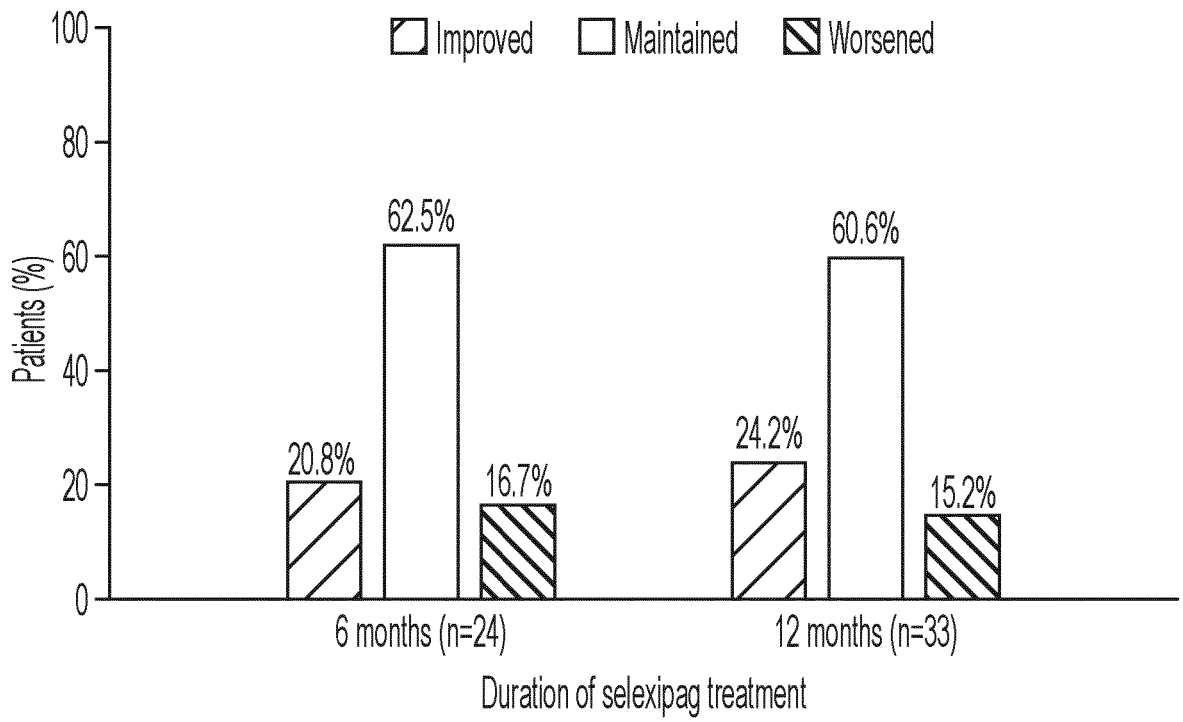
FIG. 3A is a bar graph showing the change from baseline in assessed risk (improved, maintained, or worsened) at 6 months and 12 months in patients transitioned from inhaled/oral prostacyclin pathway agents.

At baseline, 7 (19.4%) of patients who had transitioned from an oral/inhaled, non-selexipag PPA were categorized as low-risk, 27 (75.0%) were categorized as intermediate risk, and 2 (5.6%) were categorized as high risk. At 6 and 12 months (FIG. 3A), risk status was maintained in the majority of patients (63% and 61%, respectively). At 6 months, 21% had improved risk status, and 17% had worsened risk status. At 12 months, 24% had improved FC, and 15% had worsened FC.

Figure 3B:
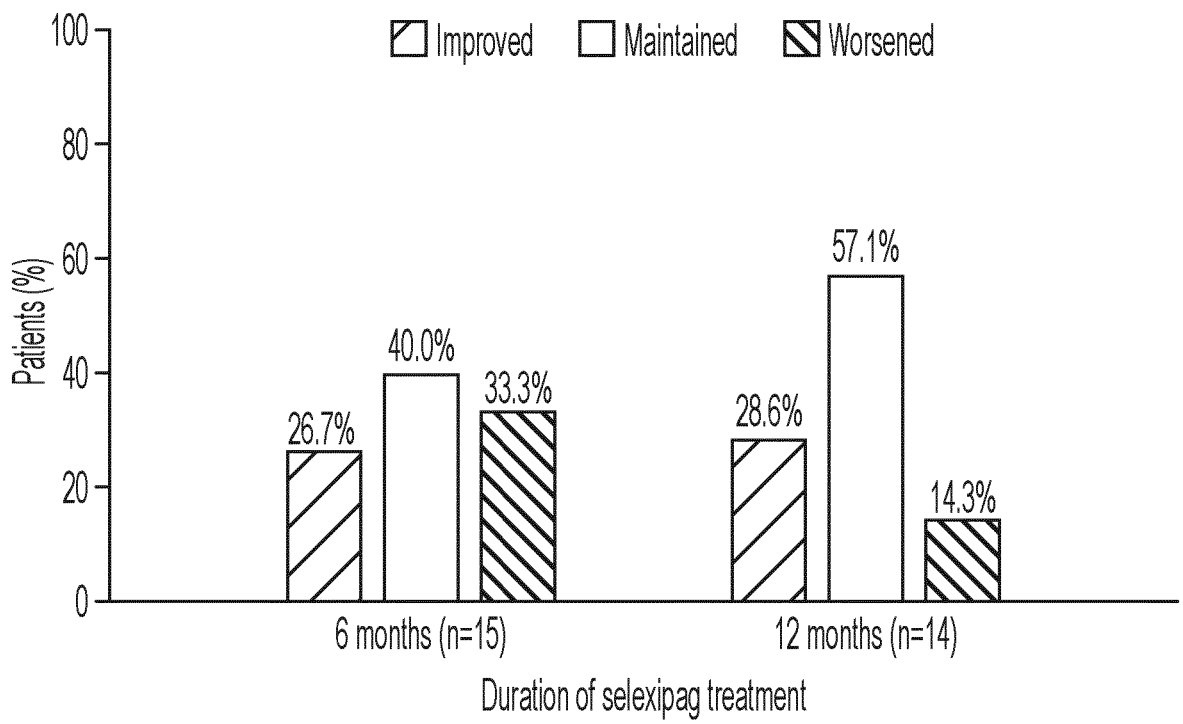
FIG. 3B is a bar graph showing the change from baseline in assessed risk (improved, maintained, or worsened) at 6 months and 12 months in patients transitioned from parenteral prostacyclin pathway agents.

At baseline, 6 (30.0%) of patients who had transitioned from a parenteral, non-selexipag PPA were categorized as low-risk, 13 (65.0%) were categorized as intermediate risk, and 1 (5.0%) was categorized as high risk. At 6 months, 67% had maintained (40%) or improved (27%) risk status, but 33% had worsened risk status (FIG. 3B). At 12 months, 86% had maintained (57%) or improved (29%) risk status, but 14% had worsened risk status.

E. Safety

Safety data were collected only for the period during which patients were enrolled. The median total duration of selexipag treatment on study was 13.7 months (IQR: 9.1-17.8 months) for all patients: 13.8 months (IQR: 9.2-17.8 months) for patients in the inhaled/oral group and 13.4 months (IQR: 6.8-15.9 months) for patients in the parenteral group.

In total, 19.6% of patients permanently discontinued selexipag because of AEs; 16.7% were patients transitioned from inhaled/oral therapy, and 25.0% were patients transitioned from parenteral therapy. Of the remaining 5 patients who discontinued selexipag, 1 discontinued because if death, 1 for a non-specified reason other than an AE and for 3 patients the reason was not reported.

The most commonly reported AE resulting in the discontinuation of selexipag was worsening pulmonary hyperten- F. Conclusions Regardless of the type of non-selexipag PPA from which patients transitioned, the majority demonstrated unchanged or improved disease 12 months after transitioning to selexipag as indicated by FC, 6MWD, and risk status.

The examples and embodiments described herein are for illustrative purposes only and various modifications or changes suggested to persons skilled in the art are to be included within the spirit and purview of this application and scope of the appended claims.

What is claimed is:

1. A method of transitioning a patient being treated for pulmonary arterial hypertension with an oral non-selexipag prostacyclin pathway agent (PPA) to selexipag, comprising administering oral selexipag to the patient at a starting dose and increasing to a highest tolerable maintenance dose that is maintained for greater than about 14 days without change or interruption, wherein the patient was taking the non-selexipag PPA for about 30 or more days at the time of selexipag initiation and stopped the non-selexipag PPA less than about 7 days before the selexipag initiation, or wherein the patient continued taking the non-selexipag PPA at the time of selexipag initiation and subsequently stopped the non-selexipag PPA.

2. The method of claim 1, wherein the starting dose is about 200 μg twice daily.

3. The method of claim 1, wherein the maintenance dose is about 1000 μg to about 1600 μg twice daily.

4. The method of claim 1, wherein the time to reach the maintenance dose is about 5 to about 10 weeks.

5. The method of claim 1, wherein the patient stopped the non-selexipag PPA less than about 7 days before the selexipag initiation.

* * * * *